(12) United States Patent
Khanzhin et al.

(10) Patent No.: US 11,142,541 B2
(45) Date of Patent: *Oct. 12, 2021

(54) PURIFICATION OF OLIGOSACCHARIDES

(71) Applicant: GLYCOM A/S, Hørsholm (DK)

(72) Inventors: Nikolay Khanzhin, Humlebæk (DK);
Markus Jondelius Hederos, Trelleborg (SE)

(73) Assignee: GLYCOM A/S, Hørsholm (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/626,122

(22) PCT Filed: Jun. 27, 2018

(86) PCT No.: PCT/IB2018/054748
§ 371 (c)(1),
(2) Date: Dec. 23, 2019

(87) PCT Pub. No.: WO2019/003133
PCT Pub. Date: Jan. 3, 2019

(65) Prior Publication Data
US 2020/0148793 A1    May 14, 2020

(30) Foreign Application Priority Data

Jun. 30, 2017 (DK) .......................... PA 2017 70522
Jun. 30, 2017 (DK) .......................... PA 2017 70523
Jun. 30, 2017 (DK) .......................... PA 201770524

(51) Int. Cl.
| | | |
|---|---|---|
| C07H 1/06 | (2006.01) | |
| B01D 61/02 | (2006.01) | |
| B01D 61/04 | (2006.01) | |
| B01D 61/58 | (2006.01) | |
| B01D 69/02 | (2006.01) | |
| B01D 69/12 | (2006.01) | |
| B01D 71/56 | (2006.01) | |
| B01D 71/58 | (2006.01) | |
| C07H 3/06 | (2006.01) | |
| C12P 19/04 | (2006.01) | |
| C08B 37/00 | (2006.01) | |
| C12P 19/12 | (2006.01) | |
| A23L 33/00 | (2016.01) | |
| C12P 19/18 | (2006.01) | |

(52) U.S. Cl.
CPC ............. *C07H 1/06* (2013.01); *A23L 33/40* (2016.08); *B01D 61/027* (2013.01); *B01D 61/04* (2013.01); *B01D 61/58* (2013.01); *B01D 69/02* (2013.01); *B01D 69/12* (2013.01); *B01D 69/125* (2013.01); *B01D 71/56* (2013.01); *B01D 71/58* (2013.01); *C07H 3/06* (2013.01); *C08B 37/0003* (2013.01); *C12P 19/04* (2013.01); *C12P 19/12* (2013.01); *C12P 19/18* (2013.01); *A23V 2002/00* (2013.01); *B01D 2315/16* (2013.01); *B01D 2325/20* (2013.01)

(58) Field of Classification Search
CPC ........... C12P 19/12; C12P 19/04; C12P 19/18; C07H 3/06; C07H 1/06; B01D 61/027; B01D 2315/16; B01D 61/145; B01D 69/12; B01D 61/04; B01D 61/58; B01D 69/02; B01D 69/125; B01D 71/56; B01D 71/58; B01D 2325/20; A23L 33/40; A23L 33/00; C08B 37/0003; A23V 2002/00
See application file for complete search history.

(56) References Cited

U.S. PATENT DOCUMENTS

| | | | |
|---|---|---|---|
| 5,827,714 A | 10/1998 | Yamamoto et al. | |
| 6,255,094 B1 | 7/2001 | Yamamoto et al. | |
| 7,521,212 B1 | 3/2009 | Morgan et al. | |
| 7,993,875 B2 | 8/2011 | Tsukamoto et al. | |
| 8,187,853 B2 | 5/2012 | Yamamoto et al. | |
| 8,372,617 B2 | 2/2013 | Yamamoto et al. | |
| 2007/0020736 A1 | 1/2007 | Samain | |
| 2012/0121788 A1 | 5/2012 | Scott et al. | |
| 2012/0184015 A1 | 7/2012 | Mine et al. | |
| 2017/0204443 A1 | 7/2017 | Baumgartner et al. | |

FOREIGN PATENT DOCUMENTS

| | | |
|---|---|---|
| EP | 0557580 A1 | 9/1993 |
| EP | 1405856 A1 | 4/2004 |
| EP | 2484686 A1 | 8/2012 |
| EP | 2526784 A1 | 11/2012 |
| EP | 2722394 A1 | 4/2014 |
| WO | 9632492 | 10/1996 |
| WO | 9815581 | 4/1998 |
| WO | 9931224 | 6/1999 |
| WO | 0104341 A1 | 1/2001 |
| WO | 2005067962 A2 | 7/2005 |
| WO | 2006034225 A2 | 3/2006 |
| WO | 2007051475 A1 | 5/2007 |
| WO | 2007101862 A1 | 9/2007 |

(Continued)

OTHER PUBLICATIONS

Antoine,, T. et al., "Highly Efficient Biosynthesis of the Oligosaccharide Moiety of the GD3 Ganglioside by Using Metabolically Engineered *Escherichia coli*," Angew. Chem. Int. Ed., 2005, vol. 44, pp. 1350-1352.

(Continued)

*Primary Examiner* — Krishnan S Menon

(74) *Attorney, Agent, or Firm* — Neal, Gerber & Eisenberg LLP

(57) ABSTRACT

The invention relates to separation of disaccharides from tri- or higher oligosaccharides by nanofiltration.

18 Claims, No Drawings

(56) References Cited

FOREIGN PATENT DOCUMENTS

| | | | |
|---|---|---|---|
| WO | 2010070104 A | 6/2010 | |
| WO | 2010116317 A1 | 10/2010 | |
| WO | 2010142305 A1 | 12/2010 | |
| WO | 2012010889 A1 | 1/2012 | |
| WO | 2012112777 A2 | 8/2012 | |
| WO | 2012156897 A1 | 11/2012 | |
| WO | 2012156898 A1 | 11/2012 | |
| WO | 2012158517 A | 11/2012 | |
| WO | 2013083623 A1 | 6/2013 | |
| WO | 2013185780 A1 | 12/2013 | |
| WO | 2014153253 A1 | 9/2014 | |
| WO | 2015036138 A1 | 3/2015 | |
| WO | 2015106943 A1 | 7/2015 | |
| WO | 2015150328 A1 | 10/2015 | |
| WO | 2016008602 A1 | 1/2016 | |
| WO | 2016063262 A1 | 4/2016 | |
| WO | 2016095924 A1 | 6/2016 | |
| WO | 2016157108 A1 | 10/2016 | |
| WO | 2016199069 A1 | 12/2016 | |
| WO | 2016199071 A1 | 12/2016 | |
| WO | 2017086443 A1 | 5/2017 | |

OTHER PUBLICATIONS

Aydogan, N. et al., "Effect of Operating Parameters on the Separation of Sugars by Nanofiltration," Separation Science and Technology, 1998, vol. 33(12), pp. 1767-1785.
Baumgärtner, F. et al., "Construction of *Escherichia coli* strains with chromosomally integrated expression cassettes for the synthesis of 20-fucosyllactose," Microbial Cell Factories, 2013, 13 pages. http://www.microbialcellfactories.com/content/12/1/40.
Cantarel, B.L. et al., "The Carbohydrate-Active EnZymes database (CAZy): an expert resource for Glycogenomics," Nucleic Acids Research, 2009, vol. 37, pp. D233-D238.
Chen, X. (2015)."Human Milk Oligosaccharides (HMOS): Structure, Function, and Enzyme-Catalyzed Synthesis," Elsevier Inc. (vol. 72), Advances in Carbohydrate Chemistry and Biochemistry, pp. 113-190. http://dx.doi.org/10.1016/bs.accb.2015.08.002.
Cobucci-Ponzano, B. et al., "b-Glycosyl Azides as Substrates for a-Glycosynthases: Preparation of Efficient a-L-Fucosynthases," Chemistry & Biology, 2009, vol. 16, pp. 1097-1108.
Córdova, A. et al., "Purification of galacto-oligosaccharides (GOS) by three-stage serial nanofiltration units under critical transmembrane pressure conditions," Chemical Engineering Research and Design, 43 pages, http://dx.doi.org/10.1016/j.cherd.2016.11.006.
Drouillard, S. et al. "Efficient synthesis of 60-sialyllactose, 6,60-disialyllactose, and 60-KDO-lactose by metabolically engineered *E. coli* expressing a multifunctional sialyltransferase from the *Photobacterium* sp. JT-ISH-224," Carbohydrate Research, 2010, vol. 345, pp. 1394-1399.
Drouillard, S. et al., "Large-Scale Synthesis of H-Antigen Oligosaccharides by Expressing Helicobacter pylori a1,2-Fucosyltransferase in Metabolically Engineered *Escherichia coli* Cells," Angew. Chem. Int. Ed. 2006, vol. 45, pp. 1778-1780.
Fierfort, N. et al., "Genetic engineering of *Escherichia coli* for the economical production of sialylated oligosaccharides," Journal of Biotechnology, 2008, vol. 134, pp. 261-265.
Gilbert, M. et al., The synthesis of sialylated oligosaccharides using CMP-Neu5Ac synthetase/sialyltransferase fusion, Nature Biotechnology, 1998, vol. 16, 99 769-772.
Goulas, A.K. et al., "Fractionation of oligosaccharides by nanofiltration," Journal of the Science of Food and Agriculture, 2003, vol. 83, pp. 675-680.
Goulas, A.K. et al., "Purification of oligosaccharides by nanofiltration," Journal of Membrane Science, 2002, vol. 209, pp. 321-335.
Han, N.S. et al., "Biotechnological production of human milk oligosaccharides," Biotechnology Advances, 2012, vol. 30, pp. 1268-1278.

Lee, W. et al., "Whole cell biosynthesis of a functional oligosaccharide, 2'-fucosyllactose, using engineered *Escherichia coli*," Microbial Cell Factories, 2012, 22 pages. https://doi.org/10.1186/1475-2859-11-48.
Lenntech. (2013) "Biotech Elements; Small Size Spiral-wound Elements for Lab Testing", 2 pages.
Li, W. et aL, "Study on nanofiltration for purifying fructo-oligosaccharides: I. Operation modes," Journal of Membrane Science, 2004, vol. 245, pp. 123-129.
Luo, J et al., "An integrated membrane system for the biocatalytic production of 30-sialyllactose from dairy by-products," Bioresource Technology, 2014, vol. 166, pp. 9-16.
Martinez-Ferez, A. et al., "Goats' milk as a natural source of lactose-derived oligosaccharides: Isolation by membrane technology," International Dairy Journal, 2006, vol. 16, pp. 173-181.
Maru, I et al., "Synthesis of Sialyllactose from N-Acetylneuraminic Acid and Lactose by a Neuraminidase from Arthrobacter ureafaciens," Biosci. Biotech. Biochem., 1992, vol. 56(10), pp. 1557-1561.
Masuda, M., et al., "Continuous Production of Sialyllactose from Colominic Acid Using a Membrane Reactor," Journal of Bioscience and Bioengineering, 2000, vol. 89(2), pp. 119-125.
Peirtsegaele, E. (2017) "Nanofiltration: The Newest Class of Membrane Filtration," MICRODYN-NADIR US, Inc. 3 pages.
Mine, T. et al., "An α2,3-Sialyltransferase from *Photobacterium* sp. JT-ISH-224 Transfers N-Acetylneuraminic Acid to Both the O-2 and O-3' Hydroxyl Groups of Lactose," Journal of Carbohydrate Chemistry, 2010, vol. 29, pp. 51-60.
Mine, T. et al., "An α2,6-sialyltransferase cloned from Photobacterium leiognathi strain JT-SHIZ-119 shows both sialyltransferase and neuraminidase activity," Glycobiology, 2010, vol. 20(2), pp. 158-165.
Murata, T. et al., "Facile enzymatic conversion of lactose into lacto-N-tetraose and lacto-N-neotetraose," Glycoconjugate Journal, 1999, vol. 16, pp. 189-195.
Ninonuevo, M.R. et al., "A Strategy for Annotating the Human Milk Glycome," J. Agric. Food Chem., 2006, vol. 54, pp. 7471-7480.
Niordvang, R. T., et al. (2015). Production of prebiotic oligosaccharides by novel enzymatic catalysis. Technical University of Denmark, Department of Chemical and Biochemical Engineering. 142 pages.
Nordvang, R.T. et al., "Separation of 3'-sialyllactose and lactose by nanofiltration: A trade-off between charge repulsion and pore swelling induced by high pH," Separation and Purification Technology, 2014, vol. 138, pp. 77-83.
Osanjo, G. et al., "Directed Evolution of the R-L-Fucosidase from Thermotoga maritima into an R-L-Transfucosidase," Biochemistry, 2007, vol. 46, pp. 1022-1033.
Priem, B. et al., "A new fermentation process allows large-scale production of human milk oligosaccharides by metabolically engineered bacteria," Glycobiology, 2002, vol. 12(4), pp. 235-240.
Sano, M. et al., "An enzyme releasing lacto-N-biose from oligosaccharides," Proc. Natl. Acan. Sci. USA, 1992, vol. 89, pp. 8512-8516.
Sano, M. et al., "Purification and Characterization of an Enzyme Releasing Lacto-N-biose from Oligosaccharides with Type 1 Chain," The Journal of Biological Chemistry, 1993, vol. 268(25), pp. 18560-18566.
Sarney, D.B. et al., "A Novel Approach to the Recovery of Biologically Active Oligosaccharides from Milk Using a Combination of Enzymatic Treatment and Nanofiltration," Biotechnology and Bioengineering, 2000, vol. 69(4), pp. 461-467.
Shoda, S. et al., "Chemo-enzymatic synthesis of novel oligo-N-acetyllactosamine derivatives having a b(1-4)-b(1-6) repeating unit by using transition state analogue substrate," Cellulose, 2006, vol. 13, pp. 477-484.
Ten Bruggencate, S.J.M. et al, "Functional role and mechanisms of sialyllactose and other sialylated milk oligosaccharides," Nutrition Reviews, 2014, vol. 72(6), pp. 377-389.
Urashima, T. et al. (2011) Nutrition and Diet Research Progress: Milk Oligosaccharides. New York: Nova Science Publishers, Inc. 92 pages.

(56) References Cited

OTHER PUBLICATIONS

Wada, J. et al., "1,2-alpha-L-Fucosynthase: A glycosynthase derived from an inverting alpha-glycosidase with an unusual reaction mechanism," FEBS Letters, 2008, vol. 582, pp. 3739-3743.

Wada, J. et al., "Bifidobacterium bifidum Lacto-N-Biosidase, a Critical Enzyme for the Degradation of Human Milk Oligosaccharides with a Type 1 Structure," Applied and Environmental Microbiology, 2008, vol. 74(13), pp. 3996-4004.

Yamamoto, T. et al., "A β-galactoside α2,6-sialyltransferase produced by a marine bacterium, Photobacterium leiognathi JT-SHIZ-145, is active at pH 8," Glycobiology, 2007, vol. 17(11), pp. 1167-1174.

Yamamoto, T. et al., "Cloning and Expression of a Marine Bacterial β-Galactoside α2,6-Sialyltransferase Gene from Photobacterium damsela JT0160," J. Biochem., 1998, vol. 123, pp. 94-100.

Yushkin, A., et al., "Improvement of MWCO determination by using branched PEGs and MALDI method," Separation and Purification Technology, 2019, vol. 211, pp. 108-116.

PURIFICATION OF OLIGOSACCHARIDES

CROSS-REFERENCE TO RELATED APPLICATION

This application is a national stage entry pursuant to 35 U.S.C. § 371 of International Application No. PCT/IB2018/054748, filed on Jun. 27, 2018, which claims priority to each of DK Patent Application No. PA 2017 70522, filed on Jun. 30, 2017, DK Patent Application No. PA 2017 70523, filed on Jun. 30, 2017, and DK Patent Application No. PA 2017 70524, filed on Jun. 30, 2017, the contents of all of which are fully incorporated herein by reference.

FIELD OF THE INVENTION

This invention relates to a method for separating tri- or higher oligosaccharides, preferably human milk oligosaccharides (HMOs), from disaccharides, preferably lactose, produced by a fermentation or enzymatic process.

BACKGROUND OF THE INVENTION

In recent years, the manufacture and commercialization of complex carbohydrates including naturally secreted oligosaccharides have increased significantly due to their roles in numerous biological processes occurring in living organisms. Secreted oligosaccharides such as human milk oligosaccharides (HMOs) are carbohydrates which have gained much interest in recent years and are becoming important commercial targets for nutrition and therapeutic industries. In particular, the synthesis of these HMOs has increased significantly due to the role of HMOs in numerous biological processes occurring in humans. The great importance of HMOs is directly linked to their unique biological activities such as antibacterial, antiviral, immune system and cognitive development enhancing activities. Human milk oligosaccharides are found to act as prebiotics in the human intestinal system helping to develop and maintain the intestinal flora. Furthermore, they have also proved to be anti-inflammatory, and therefore these compounds are attractive components in the nutritional industry for the production of, for example, infant formulas, infant cereals, clinical infant nutritional products, toddler formulas, or as dietary supplements or health functional food for children, adults, elderly or lactating women, both as synthetically composed and naturally occurring compounds and salts thereof. Likewise, the compounds are also of interest in the medicinal industry for the production of therapeutics due to their prognostic use as immunomodulators. However, the syntheses and purification of these oligosaccharides and their intermediates remained a challenging task for science.

The availability of naturally occurring sialylated human milk oligosaccharides is limited from natural sources. Mature human milk is the natural milk source that contains the highest concentrations of milk oligosaccharides (12-14 g/l), other milk sources are cow's milk (0.01 g/l), goat's milk and milk from other mammals. Approximately 200 HMOs have been detected from human milk by means of combination of techniques including microchip liquid chromatography mass spectrometry (HPLC Chip/MS) and matrix-assisted laser desorption/ionization Fourier transform ion cyclotron resonance mass spectrometry (MALDI-FT ICR MS) (Ninonuevo et al. *J. Agric. Food Chem.* 54, 7471 (2006)), from which to date at least 115 oligosaccharides have been structurally determined (Urashima et al.: *Milk Oligosaccharides*, Nova Medical Books, NY, 2011; Chen *Adv. Carbohydr. Chem. Biochem.* 72, 113 (2015)). Due to the large number of similar HMOs and their low concentrations in mammalian milk, isolation of HMOs is a difficult task even in milligram quantities. To date only analytical HPLC methodologies have been developed for the isolation of some HMOs from natural sources. It is therefore difficult to provide suitable HMO replacements in foods, particularly in infant formulae which display at least part of the entire spectrum of HMOs.

Biotechnological approaches have proved to be promising and cost-efficient for the synthesis of a variety of HMOs. Precisely, HMOs can be produced in aqueous media by fermentation of genetically modified bacteria, yeasts or other microorganisms. See, for example, WO 01/04341, WO 2007/101862, WO 2010/070104, WO 2010/142305, WO 2012/112777, WO 2014/153253, WO 2015/036138, WO 2015/150328, WO 2016/008602, EP-A-2722394, Priem et al. *Glycobiology* 12, 235 (2002), Drouillard et al. *Angew. Chem. Int. Ed.* 45, 1778 (2006), Han et al. *Biotechnol. Adv.* 30, 1268 (2012), Lee et al. *Microb. Cell Fact.* 11:48 (2012) and Baumgärtner et al. *Microb. Cell Fact.* 12:40 (2013). However, biotechnological methods provide a complex mixture in which the produced HMO is accompanied by contaminants and other impurities (of bacterial or chemical origin such as enzymes, proteins, protein fragments, endotoxins, DNA, carbohydrate by-products, salts, unreacted precursors, colour bodies, etc.) and the separation of HMO product from those contaminants and impurities is necessary. A part of the problem is to separate the HMO product from lactose, since lactose is exogenously added, usually in excess, to the culture medium as a precursor to make HMOs. The same problem applies to enzymatic (ex vivo) production of HMOs from lactose.

Aydoğan et al. (*Separ. Sci. Technol.* 33, 1767 (1998)) stated that nanofiltration is not a very suitable method for fractionation of sugars.

WO 98/15581 discloses the retention characteristics of salts and carbohydrates (lactose, sialyllactose, lacto-N-triose II, lacto-N-tetraose), and concludes that while both GE GH and GE GE polyamide membranes allow ions to pass, the GE GE membrane retains sialyllactose or similar trisaccharides more efficiently than the GE GH membrane. No conclusion about whether lactose could be separated from higher oligosaccharides was drawn.

Goulas et al. (*J. Sci. Food Agric.* 83, 675 (2003)) investigated the fractionating of commercial oligosaccharide mixtures by nanofiltration and observed that the rejection and permeate concentration values given by the membranes for the sugars during the filtration of single-sugar solutions would be not the same as if these sugars had been in a mixed solution.

WO 2005/067962 discloses the isolation of goat milk oligosaccharides comprising filtration of skimmed goat milk ultrafiltration permeate with a ceramic membrane of 1-5 kDa. Although a partial separation of salts and lactose is anticipated, the application is silent to quantify this. Nevertheless, the method further comprises active charcoal chromatography, ion exchange chromatography and electrodialysis to remove lactose and salts.

Luo et al. (*Biores. Technol.* 166, 9 (2014)) and Nordvang et al. (*Separ. Purif. Technol.* 138, 77 (2014)) tested the separation of enzymatically produced 3'-SL from lactose by nanofiltration; although a polyethersulphone (PES) membrane with a MWCO of 1000-1400 Da and a sulphonated PES membrane with a MWCO of 600-800 Da were suitable to separate the most of the lactose after diafiltration, the loss of 3'-SL was significant and its purity after separation was rather moderate, thus 3'-SL was further purified with anion exchange chromatography.

Accordingly, an improved filtration method for separating an HMO from lactose used as precursor in the fermentation or enzymatic production of said HMO is highly needed.

SUMMARY OF THE INVENTION

It is the object of the present invention to provide an improved filtration method for separating an HMO from lactose used as precursor in the fermentation or enzymatic production of said HMO.

In accordance with this invention, a method is provided for separating a tri- or higher oligosaccharide from a disaccharide dissolved in a feed solution, preferably dissolved in said feed solution, particularly in an aqueous medium from a fermentation or enzymatic process, comprising:
- contacting the feed solution with a polyamide nanofiltration membrane with a molecular weight cut-off (MWCO) of 600-3500 Da ensuring the retention of the tri- or higher oligosaccharide and allowing at least a part of the disaccharide to pass through the membrane, wherein the MgSO4 rejection factor on said membrane is 50-90%,
- a subsequent optional diafiltration with the said membrane,
- and collecting the retentate enriched in the tri- or higher oligosaccharide.

Preferably, the tri- or higher oligosaccharide comprises the disaccharide in its structure. More preferably, the tri- or higher oligosaccharide is a human milk oligosaccharide and the disaccharide is lactose.

Also preferably, the polyamide nanofiltration membrane is a thin-film composite (TFC) membrane.

Yet preferably, the polyamide nanofiltration membrane is a phenylene diamine or a piperazine membrane.

In accordance with this invention, in different embodiments, before contacting the aqueous medium with the nanofiltration membrane, one of or both the following steps are carried out:
a) the aqueous medium is clarified to remove particulates and contaminants and advantageously also cell components and any insoluble metabolites and debris from a fermentation process; and
b) substantially all proteins are removed from the aqueous medium, advantageously after the aqueous medium is clarified in step a).

DETAILED DESCRIPTION OF THE INVENTION

Terms and definitions

The term "monosaccharide" means a sugar of 5-9 carbon atoms that is an aldose (e.g. D-glucose, D-galactose, D-mannose, D-ribose, D-arabinose, L-arabinose, D-xylose, etc.), a ketose (e.g. D-fructose, D-sorbose, D-tagatose, etc.), a deoxysugar (e.g. L-rhamnose, L-fucose, etc.), a deoxy-aminosugar (e.g. N-acetylglucosamine, N-acetylmannosamine, N-acetylgalactosamine, etc.), an uronic acid, a ketoaldonic acid (e.g. sialic acid) or equivalents.

The term "disaccharide" means a carbohydrate consisting of two monosaccharide units linked to each other by an interglycosidic linkage.

The term "tri- or higher oligosaccharide" means a sugar polymer consisting of at least three, preferably from three to eight, more preferably from three to six, monosaccharide units (vide supra). The oligosaccharide can have a linear or branched structure containing monosaccharide units that are linked to each other by interglycosidic linkages.

The term "human milk oligosaccharide" or "HMO" means a complex carbohydrate found in human breast milk (Urashima et al.: *Milk Oligosaccharides*, Nova Medical Books, NY, 2011; Chen *Adv. Carbohydr. Chem. Biochem.* 72, 113 (2015)). The HMOs have a core structure being a lactose unit at the reducing end that is elongated by one or more β-N-acetyl-lactosaminyl and/or one or more β-lacto-N-biosyl units, and which core structures can be substituted by an α-L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-triose II (LNTri, GlcNAc(β1-3)Gal (β1-4)Glc), lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyl-lactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

The term "sialyl" or "sialyl moiety" means the glycosyl residue of sialic acid (N-acetyl-neuraminic acid, Neu5Ac), preferably linked with α-linkage:

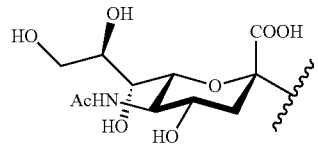

The term "fucosyl" means an L-fucopyranosyl group, preferably linked with α-interglycosidic linkage:

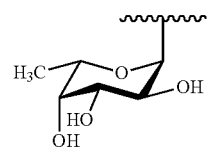

"N-acetyl-glucosaminyl" means an N-acetyl-2-amino-2-deoxy-D-glucopyranosyl (GlcNAc) group, preferably linked with β-linkage:

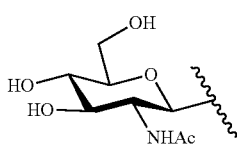

"N-acetyl-lactosaminyl" means the glycosyl residue of N-acetyl-lactosamine (LacNAc, Galpβ1-4GlcNAcp), preferably linked with β-linkage:

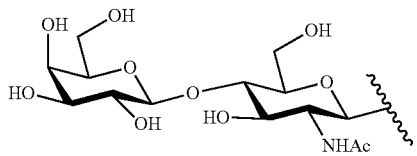

Furthermore, the term "lacto-N-biosyl" means the glycosyl residue of lacto-N-biose (LNB, Galpβ1-3GlcNAcp), preferably linked with β-linkage:

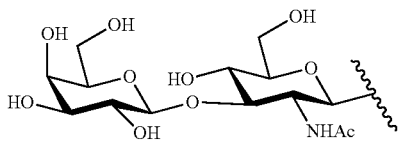

The term "aqueous medium [from a fermentation or enzymatic process]" preferably means an aqueous suspension resulting from an enzymatic or fermentation process for producing one or more hydrophilic oligosaccharides, preferably one or more HMOs and/or one or more HMO components, especially a mixture thereof.

The term "protein-free aqueous medium" preferably means an aqueous medium or broth from a fermentation or enzymatic process, which has been treated to remove substantially all the proteins, as well as peptides, peptide fragments, RNA and DNA, as well as endotoxins and glycolipids that could interfere with the eventual purification of the one or more hydrophilic oligosaccharides, especially the one or more hydrophilic HMOs and/or one or more of their components, especially the mixture thereof, from the fermentation or enzymatic process. Such removal of proteins, peptides, peptide fragments, RNA and DNA can be accomplished in a conventional manner, e.g. by ion exchange chromatography, affinity chromatography, ultrafiltration, and size exclusion chromatography.

The term "clarified aqueous medium" preferably means an aqueous medium or broth from a fermentation or enzymatic process, which has been treated to remove suspended particulates and contaminants from the process, particularly cells, cell components, insoluble metabolites and debris from a fermentation process, that could interfere with the eventual purification of the one or more hydrophilic oligosaccharides, especially one or more HMOs and/or one or more HMO components, especially mixtures thereof, from the fermentation or enzymatic process. Such a clarification treatment can be carried out in a conventional manner by centrifugation, flocculation, flocculation with optional ultrasonic treatment, gravity filtration, microfiltration, foam separation or vacuum filtration (e.g., through a ceramic filter which may include a Celite™ filter aid).

Rejection factor of a salt (in percent) is calculated as $(1-\kappa_p/\kappa_r)\cdot 100$, wherein $\kappa_p$ is the conductivity of the salt in the permeate and $\kappa_r$ is the conductivity of the salt in the retentate. The retentate concentration is practically equal to the feed concentration concerning the salt. The procedure for measuring rejection of salts is disclosed in the working examples below.

Rejection factor of a carbohydrate (in percent) is calculated as $(1-C_p/C_r)\cdot 100$, wherein $C_p$ is the concentration of the carbohydrate in the permeate and $C_r$ is the concentration of the carbohydrate in the retentate. The retentate concentration is practically equal to the feed concentration concerning the carbohydrate. One exemplary procedure for measuring rejection of a carbohydrate is disclosed in the working examples below.

Separation factor concerning two carbohydrates is calculated as $(C_{p1}/C_{r1})/(C_{p2}/C_{r2})$, wherein $C_{p1}$ and $C_{p2}$ are the concentrations of the first and the second carbohydrate, respectively, in the permeate, and $C_{r1}$ and $C_{r2}$ are the concentrations of the first and the second carbohydrate, respectively, in the retentate.

"Pure water flux" is defined as the volume of purified water (e.g. distilled water, RO water) that passes through a membrane per unit area, per unit time, and per unit of transmembrane pressure under specified conditions (at 23-25° C., 10 bar and constant cross-flow of 300 l/h). The procedure for measuring the pure water flux is disclosed in example 5 below.

Separating a Tri- or Higher Oligosaccharide from a Disaccharide

The separation and therefore the purification of valuable oligosaccharides such as human milk oligosaccharides from the medium in which they have been produced, e.g. a fermentation broth or enzymatic reaction mixture, has always been a complicated multistep process due to the presence of numerous contaminants and by-products of different physical and chemical characters. One of the most difficult problem is to separate compounds of similar nature from each other, like to separate a desired carbohydrate from other, non-desired carbohydrates.

The present inventors have surprisingly found that a nanofiltration step significantly facilitates the separation and purification of oligosaccharides, advantageously human milk oligosaccharides, from other compounds, in particular other saccharides, in a complex broth.

Accordingly, a method is provided for separating a tri- or higher oligosaccharide from a disaccharide which are dissolved in a feed solution, particularly in an aqueous medium from a fermentation or enzymatic process, comprising:

contacting the feed solution with a nanofiltration membrane with a molecular weight cut-off (MWCO) of 600-3500 Da ensuring the retention of the tri- or higher oligosaccharide and allowing at least a part of the disaccharide to pass through the membrane, wherein the active (top) layer of the membrane is composed of polyamide, and wherein the MgSO$_4$ rejection factor on said membrane is 50-90%, a subsequent optional diafiltration with said membrane, and collecting the retentate enriched in the tri- or higher oligosaccharide.

The term "ensuring the retention of the tri- or higher oligosaccharide" preferably means that, during the nanofiltration step, the tri- or higher oligosaccharides do not pass, or at least significantly do not pass, through the membrane and thus their vast majority will be present in the retentate. The term "allowing at least a part of the disaccharide to pass through the membrane" preferably means, that the disaccharide, at least partially can penetrate the membrane and be collected in the permeate. In case of high rejection (about 90%) of the disaccharide, a subsequent diafiltration with pure water may be necessary to bring all or at least the majority of the disaccharide in the permeate. The higher the disaccharide rejection the more diafiltration water is necessary for efficient separation.

The applied nanofiltration membrane shall be tight for tri- and higher oligosaccharides in order that they are efficiently retained. Preferably, the rejection of the tri- or higher oligosaccharides is more than 95%, more preferably 97%, even more preferably 99%. Membranes with MWCO of more than 3500 Da are expected to allow more or significant amount of tri-or higher oligosaccharide pass through the membrane thus show a reduced retention of tri- or higher oligosaccharide and therefore are not suitable for the purposes of the invention, and can be excluded. In the same time, membranes with MWCO of less than 600 Da can also be excluded, because—together with the retention of tri- and higher oligosaccharides—that of the mono- and disaccharides is also expected, meaning that the overall separation of the compounds would likely be poor. In this regard, it is preferred that the rejection of the disaccharide is not more than 80-90%. If the disaccharide rejection turns to be 90±1-2%, the tri- or tetrasaccharide rejection shall preferably be around 99% or higher in order to achieve a practically satisfying separation.

It has been found that the above requirements are simultaneously fulfilled when the membrane is relatively loose for $MgSO_4$, that is its rejection is about 50-90%. In this regard the above specified membrane is tight for tri- and higher oligosaccharides, and loose for mono- and disaccharides, and as well as for $MgSO_4$. Therefore, it is possible to separate e.g. lactose, which is a precursor in making human milk oligosaccharides enzymatically or by fermentation, from the human milk oligosaccharides product by nanofiltration with a good efficacy, and additionally a substantial part of divalent ions also passes to the permeate. In some embodiments, the $MgSO_4$ rejection factor is 60-90%, 70-90%, 50-80%, 50-70%, 60-70% or 70-80%. Preferably, the $MgSO_4$ rejection factor on said membrane is 80-90%. Also preferably, the membrane has a rejection factor for NaCl that is lower than that for $MgSO_4$. In one embodiment, the rejection factor for NaCl is not more than 50%. In other embodiment, the rejection factor for NaCl is not more than 40%. In other embodiment, the rejection factor for NaCl is not more than 30%. In this latter embodiment, a substantial reduction of all monovalent salts in the retentate is also achievable.

Also preferably, in some embodiments, the pure water flux of the membrane is at least 50 $l/m^2h$ (when measured at 23-25° C., 10 bar and constant cross-flow of 300 l/h). Preferably, the pure water flux of the membrane is at least 60 $l/m^2h$, at least 70 $l/m^2h$, at least 80 $l/m^2h$ or at least 90 $l/m^2h$.

The active or the top layer of nanofiltration membrane suitable for the purpose of the invention is preferably made of polyamide. Although membranes of different type seem to have promising separation efficacy, for example NTR-7450 having sulphonated PES as active layer for separating lactose and 3'-SL (Luo et al. (*Biores. Technol.* 166, 9 (2014); Nordvang et al. (*Separ. Purif. Technol.* 138, 77 (2014)), the above specified membrane used in the invention shows always better separation of lactose from an HMO. In addition, the above mentioned NTR-7450 membrane is subject to fouling, which typically results in a drop in flux, increasing the lactose rejection and therefore a reduced separation factor (see examples). Yet preferably, the polyamide membrane is a polyamide with phenylene diamine or piperazine building blocks as amine, more preferably piperazine (referred to as piperazine-based polyamide, too).

Yet preferably, the membrane suitable for the purpose of the present invention is a thin-film composite (TFC) membrane.

An example of suitable piperazine based polyamide TFC membranes is TriSep® UA60.

The claimed method applies a nanofiltration membrane characterized by some or all of the above features and thus one or more of the following benefits are provided: selectively and efficiently removes disaccharide, preferably lactose, from tri- or higher oligosaccharides, preferably HMOs, yielding an enriched tri- or higher oligosaccharide, preferably HMO, fraction; removes efficiently monovalent as well as divalent salts therefore no ion exchange step is necessary or, if desalination is still needed, the ion exchange treatment requires substantially less resin; higher flux during the nanofiltration can be maintained compared to other membranes used for the same or similar purpose in the prior art, which reduces the operation time; the membrane applied in the claimed method is less prone to getting clogged compared to the prior art solutions; the membrane applied in the claimed can be cleaned and regenerated completely therefore can be recycled without substantial reduction of its performance.

The nanofiltration membrane defined in the method of the invention is more beneficial compared to the prior art membranes used for the same or similar purpose as that of the present invention. Specifically, ceramic membrane of 1 kDa, like the one mentioned in WO 2005/067962, shows poor separation over lactose and is prone to getting clogged; polyvinylidene fluoride (PVDF) membrane of Luo et al. or Nordvang et al. (ETNA01PP, MWCO: 1000 Da, Alfa Laval) rejects tri- to hexasaccharides less efficiently and the separation factor over lactose is substantially lower; sulphonated PES membrane of Luo et al. or Nordvang et al. (NTR-7450, MWCO: 600-800, Nitto-Denko), besides showing lower separation factor of tri- to hexasaccharides over lactose, gets easily clogged; GE GE (polyamide, MWCO: 1000 Da) and GE GH (polyamide, MWCO: 2500 Da) membranes of WO 98/15581, besides showing lower separation factor of tri- to hexasaccharides over lactose, operate at lower flux and retain higher amount of salts in the permeate due to high NaCl rejection factor.

Accordingly, in one embodiment, a method is provided for separating a tri- or higher oligosaccharide from a disaccharide which are dissolved in a feed solution, particularly in an aqueous medium from a fermentation or enzymatic process, comprising:

contacting the feed solution with a piperazine-based polyamide nanofiltration membrane with a molecular weight cut-off (MWCO) of 1000-3500 Da ensuring the retention of the tri- or higher oligosaccharide and allowing at least a part of the disaccharide to pass through the membrane, wherein the $MgSO_4$ rejection factor on said membrane is 80-90%, and wherein the NaCl rejection factor on said membrane is lower than that for $MgSO_4$, and/or the pure water flux value of said membrane is at least 50 $l/m^2h$, a subsequent optional diafiltration with said membrane, and collecting the retentate enriched in the tri- or higher oligosaccharide.

Preferably, the NaCl rejection factor of the membrane is at most the half of the $MgSO_4$ rejection factor.

To achieve all the benefits mentioned above, the nanofiltration membrane to be applied in the claimed invention, preferably:

is a piperazine-based polyamide membrane with a MWCO of 1000-3500 Da,
has a MgSO4 rejection of 50-90%, preferably 80-90%,
has a NaCl rejection of not more than 30%, and
has a pure water flux value of at least 50 l/m²h, preferably 90 l/m²h.

Also in a preferred embodiment, the structure of the tri- or higher oligosaccharide comprises the structure of the disaccharide, which disaccharide is to be separated from the tri- or higher oligosaccharide by the method of invention. Accordingly, the tri- or higher oligosaccharides are derivatives of the disaccharide, namely they are glycosylated variants of that particular disaccharide. If the disaccharide is glycosylated by adding one monosaccharide unit, it results in a trisaccharide comprising the disaccharide moiety; if the disaccharide is glycosylated by adding two monosaccharide units, it results in a tetrasaccharide comprising the disaccharide moiety; etc. The matching combinations of the disaccharide and the tri- or higher oligosaccharide are due to the practical reason that the tri- or higher oligosaccharides are produced from the disaccharide as a precursor by chemical, enzymatic or fermentative ways, especially enzymatically or by fermentation, and the disaccharide left in the reaction mixture as unreacted or because it was added in excess.

According to a more preferred embodiment, the disaccharide is lactose and the tri- or higher oligosaccharide is a glycosylated lactose, preferably a fucosylated, sialylated, N-acetylglucosaminylated, lacto-N-biosylated and/or N-acetyllactosaminylated lactose, more preferably a human milk oligosaccharide (HMO). In one embodiment, the HMO is a neutral HMO. The neutral HMO is, in one aspect, a fucosylated HMO, preferably selected from the list consisting of 2'-FL, 3-FL, DFL, LNFP-I, LNFP-II, LNFP-III and LNFP-V, more preferably 2'-FL, 3-FL and DFL; in another aspect, the neutral HMO is a non-fucosylated neutral HMO, preferably selected from the list consisting of lacto-N-triose II (GlcNAcβ1-3Galβ1-4Glc), LNT, LNnT, LNH, LNnH, pLNH I, pLNH II (Galβ1-3GlcNAcβ1-3Galβ1-3GlcNAcβ1-3Galβ1-4Glc) and pLNnH (Galβ1-4GlcNAcβ1-3Galβ1-4GlcNAcβ1-3Galβ1-4Glc), more preferably lacto-N-triose II, LNnT, pLNnH, LNT and pLNH II. In other embodiment, the HMO is a sialylated (charged) HMO, preferably selected from the list consisting of 3'-SL, 6'-SL, FSL, LST a, LST b, LST c and DS-LNT, preferably 3'-SL and 6'-SL.

Also in a preferred embodiment, the separation factor of a disaccharide over a tri- or higher oligosaccharide is more than 5, preferably more than 10, more preferably more than 25, even more preferably more than 100. Especially, the separation factor of lactose over a human milk oligosaccharide is more than 10, preferably more than 25, more preferably more than 50, even more preferably more than 100.

Yet preferably, the separation factor of a disaccharide over a trisaccharide is more than 5, preferably more than 10, more preferably more than 25. Especially, the separation factor of lactose over LNTri II is more than 10, preferably more than 20, more preferably more than 30. The separation factor of lactose over 3'-SL or 6'-SL is more than 20, preferably more than 50.

Yet preferably, the separation factor of a disaccharide over a tetrasaccharide is more than 25, preferably more than 50, more preferably more than 100. Especially, the separation factor of lactose over LNT or LNnT is more than 30, more preferably more than 50.

Yet preferably, the separation factor of a disaccharide over a hexasaccharide is more than 100. Especially, the separation factor of lactose over pLNnH or pLNH II is more than 150, more preferably more than 250.

The method of the invention can be conducted under conditions used for conventional nanofiltration with tangential flow or cross-flow filtration with positive pressure compared to permeate side followed by diafiltration where both operations could be performed in a batch mode or preferably in continuous mode. The optional diafiltration is conducted by adding pure water to the retentate after the nanofiltration step disclosed above and continuing the filtration process with constant removal of permeate under the same or similar conditions as nanofiltration. The preferred mode of water addition is continuous, i.e. the addition flow rate is matching approximately the permeate flow rate.

The pH of the feed solution applied for the NF separation according to the present invention is, preferably, not higher than 7, more preferably between 3 and 7, even more preferably around 4 and 5, or 5 and 6. A low pH may adversely influence the membrane and the solute properties.

The convenient temperature range applied is between 10 and 80° C. Higher temperature provides a higher flux and thus accelerates the process. The membrane is expected to be more open for flow-through at higher temperatures, however this doesn't change the separation factors significantly. A preferred temperature range for conducting the nanofiltration separation according to the invention is 20-45° C.

A preferred applied pressure in the nanofiltration separation is about 2-50 bars, such as 10-40 bars, the higher the pressure the higher the flux.

The one or more tri- or higher oligosaccharides, preferably HMOs, separated from a disaccharide, preferably lactose, and mono- and divalent salts and therefore purified by the method of invention can then be isolated from the aqueous retentate and from the optional the aqueous wash in a conventional manner, e.g. by evaporation, spray-drying, freeze-drying, crystallization or lyophilisation.

HMOs can be produced from lactose in a conventional manner enzymatically and/or by fermentation of genetically transformed bacteria in an aqueous medium or broth. In this regard, see for example WO 2007/101862, WO 2010/070104, WO 2010/142305, WO 2012/158517, EP-A-1405856, WO 01/04341, WO 2016/008602, WO 2012/156898, WO 2012/156897, WO 2016/063262, WO 2016/157108, WO 2016/199071, Priem et al. *Glycobiology* 12, 235 (2002), Drouillard et al. *Angew. Chem. Int. Ed.* 45, 1778 (2006), Han et al. *Biotechnol. Adv.* 30, 1268 (2012), Lee et al. *Microb. Cell Fact.* 11:48 (2012) and Baumgärtner et al. *Microb. Cell Fact.* 12:40 (2013).

In carrying out this invention, an aqueous feed medium, which can be obtained directly from an enzymatic or, preferably, a fermentation process, particularly from bacterial, e.g. *E. coli*, or yeast fermentation, and which contains one or more tri- or higher oligosaccharides, preferably HMOs, can be optionally treated by the following steps:

i) clarifying the aqueous medium to remove suspended particulates and contaminants, particularly cells, cell components, insoluble metabolites and debris from a fermentation process; and/or ii) removing substantially all the proteins, as well as peptides, amino acids, RNA and DNA and any endotoxins and glycolipids that could interfere with the subsequent purification step, from the aqueous medium, preferably after clarifying it.

In step i), the aqueous medium, which contains tri- or higher oligosaccharides, preferably HMO(s), is clarified in a conventional manner, e.g. by centrifugation or ultrafiltration. Preferably the aqueous medium is first flocculated and then centrifuged or filtered to remove any remaining insoluble particulates and contaminants, as well as cells and cell components and insoluble metabolites and debris.

In step ii), proteins and related impurities are removed from the aqueous medium in a conventional manner, e.g. by a second ultrafiltration step or tangential flow ultrafiltration.

According to steps i) or ii), the broth obtained from fermentation is subjected to ultrafiltration. The fermentation broth typically contains, besides the produced tri- or higher oligosaccharides, preferably one or more HMOs, the biomass of the cells of the used microorganism together with proteins, protein fragments, DNA, endotoxins, biogenic amines, inorganic salts, unreacted carbohydrate acceptor such as lactose, sugar-like by-products, monosaccharides, colorizing bodies, etc. The ultrafiltration step is to separate the biomass and, preferably, also high molecular weight suspended solids from the soluble components of the broth which pass through the ultrafiltration membrane in the permeate. This UF permeate (UFP) is an aqueous solution containing the produced tri- or higher oligosaccharide(s), preferably HMO(s).

Any conventional ultrafiltration membrane can be used having a molecular weight cut-off (MWCO) range between about 1 and about 500 kDa, such as 10-250, 50-100, 200-500, 100-250, 5-100, 5-50, 10-25, or any other suitable sub-ranges. The membrane material can be a ceramic or made of a synthetic or natural polymer, e.g. polysulfone, polypropylene, cellulose acetate, cellulose or polylactic acid. The ultrafiltration step can be applied in dead-end or cross-flow mode. These steps may comprise more than one ultrafiltration step using membranes with different MWCO, e.g. using two ultrafiltration separations wherein the first membrane has a higher MWCO than that of the second membrane. This arrangement may provide a better separation efficacy of the higher molecular weight components of the broth. After this separation step a typical permeate contains compounds that have a molecular weight lower than the MWCO of the second membrane, including the tri- or higher oligosaccharide(s), preferably HMO(s), of interest.

EXAMPLES

Example 1—Determination of a Substance Rejection Factor on a Membrane

The NaCl and MgSO$_4$ rejection on a membrane is determined as follows: in a membrane filtration system, a NaCl (0.1%) or a MgSO$_4$ (0.2%) solution is circulated across the selected membrane sheet (for Tami: tubular module) while the permeate stream is circulated back into the feed tank. The system is equilibrated at 10 bars and 25° C. for 10 minutes before taking samples from the permeate and retentate. The rejection factor is calculated from the measured conductivity of the samples: $(1-\kappa_p/\kappa_r)\cdot 100$, wherein $\kappa_p$ is the conductivity of NaCl or MgSO$_4$ in the permeate and $\kappa_r$ is the conductivity of NaCl or MgSO$_4$ in the retentate.

| membrane | active layer | MWCO | NaCl rej. factor supplier spec. | NaCl rej. factor lab. measurement | MgSO$_4$ rej. factor supplier spec. | MgSO$_4$ rej. factor lab. measurement |
|---|---|---|---|---|---|---|
| Trisep UA60 | piperazine-PA | 1000-3500 | — | 10% | 80% | 81-89% |
| GE GH | PA | 2500 | — | 81% | — | 76% |
| NTR-7450 | sulph. PES | 600-800 | 50% | 56% | — | 32% |
| Tami | ceramic | 1000 | — | — | — | 0% |

A carbohydrate rejection factor is determined in a similar way with the difference that the rejection factor is calculated from the concentration of the samples (determined by HPLC): $(1-C_p/C_r)\cdot 100$, wherein $C_p$ is the concentration of the carbohydrate in the permeate and $C_r$ is the concentration of the carbohydrate in the retentate.

Example 2

LNnT was made by fermentation using a genetically modified E. coli cell of LacZ$^-$, LacY$^+$ phenotype, wherein said cell comprises a recombinant gene encoding a β-1,3-N-acetyl-glucosaminyl transferase which is able to transfer the GlcNAc of UDP-GlcNAc to the internalized lactose, a recombinant gene encoding a β-1,4-galactosyl transferase which is able to transfer the galactosyl residue of UDP-Gal to the N-acetyl-glucosaminylated lactose, and genes encoding a biosynthetic pathway to UDP-GlcNAc and UDP-Gal. The fermentation was performed by culturing said cell in the presence of exogenously added lactose and a suitable carbon source, thereby producing LNnT which was accompanied by lacto-N-triose II, pLNnH and lactose in the fermentation broth. The broth was subjected to a standard cell removal operation by ultrafiltration (UF) (Kerasep ceramic membrane, pore size 50 nm or MWCO ca. 300 kDa). A portion of the obtained UF permeate (19.686 kg, containing 301 g of LNnT, 36 g of pLNnH, 113 g of lactose and 66 g of lacto-N-triose II) was subjected to cross-flow nanofiltration through Trisep TurboClean-UA60-1812 membrane (spiral wound, area 0.23 m$^2$) with nominal MW cut-off 1000-3500 Da (measured MgSO$_4$ rejection is 89%) installed in a MMS SW18 membrane filtration system at initial P=10 bar and T=20° C. with a cross-flow of approximately 300 1/h and initial permeate flux 38.3 l/m$^2$h. When the retentate volume was reduced approximately by half, the pressure was adjusted to 20 bars. When the permeate flux was reduced to 6 l/m$^2$h and retentate volume was reduced to ca 2.2 l (17 l of permeate was collected), continuous addition of fresh water (37 l) initiated at the flow rate matching approximately the permeate flow rate (flux 5-10 l/m$^2$h). After completion of the water addition, the obtained retentate was further concentrated to ca. 1.5 l at P=25 bars until the permeate flux dropped down to ca. 5 l/m$^2$ h. Samples of permeate and retentate were periodically collected and analysed for conductivity, pH and oligosaccharide concentrations by HPLC (see table below).

| permeate volume (l) | DF water (l) | estimated retentate volume (l) | lactose g/l | lacto-N-triose II g/l | LNnT g/l | p-LNnH g/l | conductivity mS/cm | pH |
|---|---|---|---|---|---|---|---|---|
| 0 | 0 | 19.2 | 5.90 | 3.42 | 15.69 | 1.89 | 8.45 | 5.90 |
| 9.8 | 0 | 9.6 | 11.01 | 7.60 | 35.18 | 4.84 | 11.05 | |
| 16.6 | 0 | 2.8 | 28.76 | 22.69 | 107.20 | 15.88 | 14.67 | 5.72 |
| 24.4 | 7 | 2 | 17.96 | 28.05 | 145.83 | 22.70 | 6.97 | |
| 34.4 | 16.5 | 1.5 | 4.14 | 30.01 | 171.76 | 28.30 | 2.31 | 5.77 |
| 44.4 | 27 | 2 | 0.35 | 21.02 | 129.36 | 19.78 | 1.33 | |
| 54.8 | 37 | 1.5 | 0 | 25.38 | 169.31 | 25.02 | 0.83 | |
| combined permeate: 55 l | | | 2.64 | 0.62 | 0.63 | 0.02 | 3.65 | |

The results show that lactose was not detected in the final retentate, the total salt content was reduced by >99% based on conductivity, while most of LNnT and pLNnH were kept in the retentate (84% and practically 100%, respectively). With regard to the total solids, its LNnT content in the feed was enriched from 33% to 71% in the obtained retentate.

Example 3

A feed solution containing LNnT, pLNnH, lacto-N-triose II and lactose, obtained from a fermentation broth after ultrafiltration (see Example 2) was equilibrated in a membrane filtration system with Trisep UA60 membrane for at least 10 min at 20° C., 20 bars, and a cross-flow of 300 l/h. During equilibration the permeate stream was circulated back into the feed tank. Samples of the obtained solution in the feed tank (retentate) and permeate were taken simultaneously for analytical characterization. Then the system was equilibrated again at 10 bars before taking corresponding analytical samples. Following this, diafiltration was conducted (see conditions in the table below) as described in Example 2. Oligosaccharide rejection factors and separation factors were calculated as given above.

Example 4

Flat sheet membranes Trisep UA60 (piperazine PA, MWCO 1000-3500 Da, measured $MgSO_4$ rejection is 89%) and Nitto-Denko NTR-7450 (sulphonated polyethersulphone, MWCO 600-800, measured $MgSO_4$ rejection is 32%) were cut into round pieces (d=20 cm, active membrane area 280 $cm^2$ for each sheet) and installed into a cross-flow flat sheet cell of the MMS SW18 membrane filtration system with 3 independent permeate stream outlets. The feed was circulated across installed membranes with approximately 300 l/h cross-flow rate with permeate streams from each membrane circulated back into the feed tank. In each run the system was equilibrated at selected pressure and temperature for at least 10 min before taking permeate and retentate analytical samples.

The feed was prepared as follows: crude LNnT solid sample was obtained from fermentation broth after cell removal by UF (15 kDa), NF with diafiltration, decolouration with activated charcoal and freeze-drying. The obtained solid contained LNnT (54.6%), lactose (9.86%), lacto-N-triose II (7.32%) and pLNnH (8.67%, all by weight), from which 41 g was dissolved in 2050 g of water, obtaining a solution having a pH of 5.71 and conductivity of 0.825 mS/cm.

Oligosaccharide concentration were determined by HPLC, and rejection and separation factors were calculated.

| | volume (l) | P (bar) | T (° C.) | flux (l/m²h) | lactose g/l | lacto-N-triose II g/l | LNnT g/l | p-LNnH g/l |
|---|---|---|---|---|---|---|---|---|
| retentate | 0 | 20 | 20 | 75.4 | 6.22 | 3.58 | 16.14 | 2.01 |
| permeate | 0 | | | | 0.72 | 0.19 | 0.02 | 0.00 |
| rejection factor | | | | | 88.44% | 94.78% | 99.89% | 100% |
| sep. factor over lactose | | | | | | 2.2 | 105 | |
| retentate | 0 | 10 | 20 | 38.3 | 5.94 | 3.60 | 16.10 | 2.08 |
| permeate | 0 | | | | 0.86 | 0.23 | 0.04 | 0.00 |
| rejection factor | | | | | 85.48% | 93.54% | 99.76% | 100% |
| sep. factor over lactose | | | | | | 2.2 | 60 | |
| retentate | 9.81 | 10 | 16 | 16.1 | 11.01 | 7.60 | 35.18 | 4.84 |
| permeate | 9.81 | | | | 2.30 | 0.67 | 0.15 | 0.00 |
| rejection factor | | | | | 79.09% | 91.21% | 99.59% | 100% |
| sep. factor over lactose | | | | | | 2.4 | 51 | |
| retentate | 16.61 | 20 | 25.5 | 6.1 | 28.76 | 22.69 | 107.20 | 15.88 |
| permeate | 16.61 | | | | 9.23 | 0.56 | 0.83 | 0.04 |
| rejection factor | | | | | 67.90% | 97.55% | 99.22% | 99.72% |
| sep. factor over lactose | | | | | | 13 | 41 | 115 |

| | | | Trisep UA60 rejection and separation factor over lactose | | | | NTR-7450 rejection and separation factor over lactose | | | |
|---|---|---|---|---|---|---|---|---|---|---|
| T °C | P bar | flux l/m²h | lactose | lacto-N-triose II | LNnT | pLNnH | lactose | lacto-N-triose II | LNnT | pLNnH |
| 24.5 | 2 | 9 | 91.4% | 99.71% | 99.78% | 99.97% | 92.02% | 99.41% | 99.66% | 99.95% |
| | | | n/a | 30 | 39 | 287 | n/a | 14 | 23 | 160 |
| 23.6 | 10 | 55.30 | 96.8% | 99.90% | 99.91% | 99.98% | 97.43% | 99.84% | 99.88% | 100% |
| | | | n/a | 32 | 36 | 160 | n/a | 16 | 21 | |
| 27 | 30 | 116.6 | 93.6% | 99.81% | 99.88% | 100% | 98.52% | 99.85% | 99.92% | 100% |
| | | | n/a | 34 | 53 | | n/a | 10 | 18 | |
| 39.4 | 2 | 9.1 | 84.5% | 99.45% | 99.70% | 99.94% | 96.66% | 99.80% | 99.85% | 99.98% |
| | | | n/a | 28 | 21 | 259 | n/a | 16 | 22 | 167 |
| 39.9 | 10 | 59.4 | 93.1% | 99.84% | 99.87% | 100% | 99.36% | 99.97% | 99.97% | 100% |
| | | | n/a | 42 | 53 | | n/a | 21 | 21 | |
| 40 | 30 | 136.1 | 88.2% | 99.64% | 99.80% | 100% | 99.43% | 99.97% | 99.97% | 100% |
| | | | n/a | 33 | 59 | | n/a | 19 | 19 | |

The data show that the NTR membrane became tight for lactose at higher operation temperature.

Example 5

The nanofiltration membranes are, in general, subject to fouling due to the presence of larger molecules in the feed solution like peptide fragments, lipids, anti-foam, etc., which causes a drop in flux and/or decrease the separation factor. The purpose of this investigation is how the membranes can be cleaned and regenerated.

Flat sheet membranes (d=20 cm, active membrane area 280 cm² for each sheet) were installed into a cross-flow flat sheet cell of the MMS SW18 membrane filtration system. Pure water was equilibrated at 10 bars and 23-25° C. with constant cross-flow (300 l/h) for at least 10 min. Then small portion (5-30 ml) of permeate fractions were collected and exact mass or volume was measured. Flux was calculated according to the following formula: $F=V/(t \cdot A)$ where V is the collected permeate volume in litres, t is the time required to collect the measured volume in hours and A is the membrane area in m².

The following pure water flux values were measured:

| membrane | active layer | MWCO | flux (l/m²h) |
|---|---|---|---|
| Trisep UA60 | piperazine-PA | 1000-3500 | 100.8 |
| GE GH | PA | 2500 | 17 |
| NTR-7450 | sulph. PES | 600-800 | 99.6 |

Then, for the Trisep UA60 and Nitto-Denko NTR-7450 membranes, water was replaced by the feed solution disclosed in Example 4 and the flux was measured under the same conditions.

Then the membranes were washed with pure water (cleaning in place, CIP1), and water flux was re-measured.

Following this, the membranes were washed with an aqueous cleaning solution containing 0.1% sodium dodecyl sulphate, 0.5% EDTA and 0.5% sodium tripolyphosphate (cleaning in place, CIP2, 30 min, 5 bar, 20-25° C.), and water flux was remeasured.

The data show that the NTR-7450 membrane is more prone to be fouled than Trisep UA60. Furthermore, while pure water washing regenerated the Trisep UA60 membrane to reach 85% of the original water flux, it was inefficient to do so for the NTR-7450 membrane. In addition, whereas a detergent containing cleaning solution completely cleaned the Trisep UA60 membrane, the NTR-4750 membrane was regenerated only partially.

| | flux (l/m²h) | |
|---|---|---|
| | Trisep UA60 | NTR-7450 |
| initial water flux | 100.8 | 99.6 |
| flux with feed solution | 55.1 | 30.3 |
| water flux after CIP1 | 85.4 | 23.9 |
| after CIP1 relative to initial | 85% | 24% |
| water flux after CIP2 | 119 | 71.3 |
| after CIP2 relative to initial | 118% | 72% |

Example 6

Properties of flat sheet membranes Trisep UA60 (piperazine PA, MWCO: 1000-3500 Da), GE GH (PA, MWCO: 2500), GE GE (PA, MWCO: 1000) and Alfa Laval ETNAO1PP (PVDF, MWCO: 1000) were investigated in an MMS membrane filtration system with 3 independent permeate stream outlets. A feed solution containing LNnT, pLNnH, lacto-N-triose II and lactose, obtained from a fermentation broth after ultrafiltration (see Example 2) was circulated across the installed membranes with approximately 300 l/h cross-flow rate with permeate streams from each membrane circulated back into the feed tank. In each run the system was equilibrated at selected pressure and temperature for at least 10 min before taking permeate and retentate analytical samples. Conditions: membrane area 0.0028 m²; temperature 20° C.; transmembrane pressure 5-8 bar. Concentration of each compound in the permeate and the retentate was determined by HPLC. The following table contains the measured average flux and the estimated rejection factors:

| membrane | average flux (l/m²h) | lactose rejection factor | lacto-N-triose II rejection factor | LNnT rejection factor | pLNnH rejection factor |
|---|---|---|---|---|---|
| Trisep UA60 | 7.6 | 80.77% | 96.47% | 99.86% | 100% |
| GE GH | 3.6 | 61.98% | 92.89% | 96.12% | 99.77% |
| GE GE | 4.1 | 63.25% | 88.01% | 95.53% | 99.61% |
| ETNA01PP | 30 | 18.34% | 33.72% | 55.54% | 70.78% |

The data show that the ETNA01PP membrane, in spite of the remarkable flux, was too loose for di- to hexasaccharides and the separation factors over lactose were rather low. As to the polyamide membranes, they showed good separation factors over lactose, however the piperazine-based Trisep UA 60 membrane was superior for the tetra- and hexasaccharide. In addition, the higher operation flux makes the Trisep membrane more beneficial for industrial application over the GE membranes.

Example 7—LST c Production Catalysed by an α2,6-transsialidase with Continuous Lactose Removal 6'-SL Na-salt (80.0 g) and LNnT (60.0 g) were dissolved in deionized water (860 g), and the pH was adjusted to 5.0 with few drops of acetic acid. α2,6-Transsialidase (A218Y-N222R-G349S-S412P-D451K mutant of *P. leiognathi* JT-SHIZ-119 sialyl transferase truncated by its signal peptide (Δ2-15), the positions of mutations are according to SEQ ID No. 1, see WO 2016/199069) was added in two portions (50 mg at the start and 100 mg after 4 hrs) and the obtained solution was agitated at ambient temperature for 21 hrs to give an equilibrated mixture of 6'-SL, LNnT, LST c and lactose with ca. 38% conversion. The obtained solution was subjected to diafiltration (DF) in the cross-flow MMS SW18 filtration system with installed Trisep UA60 membrane (piperazine PA, MWCO 1000-3500 Da, measured $MgSO_4$ rejection is 89%, spiral-wound, size 1812, area 0.23 $m^2$) at p=15-20 bar and T=25-30° C. with DF water (flow rate in the range of 3-4.5 l/h, matching approximately the permeate flow rate). During the process, additional amount of enzyme was added periodically by small portions (7×50 mg, 300 mg in total). pH was measured periodically and adjusted if necessary by adding small amount of sodium acetate to keep it in the range of 4.5-5.5. After consumption of 25 l of water, the permeate collection was paused overnight while keeping the reaction mixture circulating slowly in the system at low temperature (+8° C.). Next day DF continued with another 25 l of water under the same conditions. The obtained retentate was pumped out from the system (746 g) and the remaining dead volume was removed by washing with two portions of water (2×350 ml). The obtained diluted retentate (1448 g) was heated up to 85° C. in 30 min. The obtained suspension was allowed to cool, treated with charcoal, filtered and the filtrate was concentrated and freeze-dried to give 83.54 g of a colourless solid. Analytical samples were periodically taken and analysed by HPLC. The obtained amounts and conversion are summarized in the table below.

|  | Volume/mass | 6'-SL | lactose | LST c | LNnT | conversion |
|---|---|---|---|---|---|---|
| Initial | 950 ml | 80 g | — | — | 60 g |  |
| MW (Da) |  | 655.5 (Na-salt) | 342 | 997 | 707 |  |
| t = 2 min (mmol) | 1000 ml | 125 | — | — | 82.38 |  |
| t = 21 h (before DF, mmol) | 1000 ml | 97.8 | 31.1 | 31.1 | 51.26 | 37.9% |
| permeate 1, 0-25 l (mmol) | 25 l | 1.78 | 41.41 | 2.63 | 4.44 |  |
| permeate 2, 25-50 l (mmol) | 25 l | 0.89 | 9.82 | 1.72 | 1.94 |  |
| combined permeate (mmol) | 50 l | 2.68 | 51.23 | 4.35 | 6.38 |  |
| final diluted retentate after DF with 50 l water (mmol) | 1448 g | 34.46 | 0 | 46.57 | 10.30 |  |
| permeate + retentate (mmol) |  | 37.14 | 51.23 | 50.92 | 16.68 | 75.4% |

The data show that the membrane efficiently separated lactose, a disaccharide, from 6'-SL, a trisaccharide: while lactose could be completely removed from the retentate by diafiltration, the vast majority of 6'-SL left in the retentate (approx. 93% of the unreacted 6'-SL).

Example 8

6'-SL was made by fermentation using a genetically modified *E. coli* cell of LacZ⁻, LacY⁺ phenotype carrying heterologous neuBCA, wherein said cell comprises a recombinant gene encoding an α-2,6-sialyl transferase which is able to transfer the sialic acid of GMP-sialic acid to the internalized lactose, and deleted or inactivated nanKETA. The fermentation was performed by culturing said cell in the presence of exogenously added lactose and a suitable carbon source, thereby producing 6'-SL. The obtained fermentation broth containing 6'-SL (ca. 600 l) was subjected to cell removal by ultrafiltration/diafiltration (ceramic membrane, MWCO 15 kDa), followed by concentration by nanofiltration (MWCO 150-300 Da). In one experiment, a part of the obtained NF retentate containing 6'-SL (39.21, 6'-SL=110.2 g/l) was subjected to constant volume diafiltration with ca. 400 l of water in a NF pilot system equipped with three 1 kDa ceramic membranes (Tami INSIDE CéRAM 8-channel, size 1178×25 mm) to give a retentate (58 l, 6'-SL content: 0.9 kg) and a permeate (398 l, 6'-SL content: 3.1 kg). In other experiment, a similar NF was performed on a lab scale using 600×10 mm Tami 1 kDa membrane. A substantial reduction of pure water flux was observed from an initial flux of 136 $l/m^2$ h at TMP=6 bar to 4.1 $l/m^2$ h at TMP=10 bar. The $MgSO_4$ rejection was substantially increased as well from 0% (initial) to 80% (at the end of procedure), indicating fouling that could not be removed by water cleaning.

The data show that 1 kDa ceramic membrane is too open to be used as a NF membrane, in addition it easily gets clogged which adversely affects the membrane's separation properties.

Example 9

3-FL was made by fermentation using a genetically modified *E. coli* cell of LacZ⁻, LacY⁺ phenotype, wherein said cell comprises a recombinant gene encoding an α-1,3-fucosyl transferase which is able to transfer the fucose of GDP-fucose to the internalized lactose and genes encoding a biosynthetic pathway to GDP-fucose. The fermentation was performed by culturing said cell in the presence of exogenously added lactose and a suitable carbon source, thereby producing 3-FL which was accompanied with unreacted lactose in the fermentation broth. The fermentation broth (13818 g) was subjected to UF (15 kDa, Tami INSIDE CéRAM membrane with 39 channels, size 1178×25 mm, area 0.5 $m^2$) with diafiltration (13 l of water) to give an UF permeate (22602 g) containing lactose (9.70 g/l) and 3-FL (23.9 g/l) with a calculated lactose/3-FL ratio of 0.43 (conductivity 6.31 mS/cm). The obtained UF permeate was pH-adjusted with acetic acid to pH=3.8 followed by NF with Trisep UA60 membrane (spiral wound, size 1812, area 0.23 $m^2$) started at TMP=30 bar with increase of TMP to 38 bar after collecting 20 l of NF permeate. The obtained intermediate NF retentate had a conductivity of 6.8 mS/cm. The initial permeate flux of 36 $l/m^2h$ was decreased to 4 $l/m^2$ h at this point. Diafiltration initiated with continuous addition of water at 2.7 l/h. Total of 40 l of DF water was used. The obtained NF/DF retentate was pumped out from the system (2027 g) followed by water washes to give 2762 g of the final retentate containing 9.88 g/l of lactose and 135.90 g/l of 3/FL, calculated lactose/3FL ratio=0.07. Calculated yields in the NF/DF retentate: 3-FL 72%, lactose 13%. Conductivity in the final retentate was substantially reduced to 0.67 mS/cm indicating >95% salts removal.

The combined NF/DF permeate (61 L) was re-processed by NF/DF as above with 20 l of diafiltration water to give a second NF/DF retentate (1704 g) containing 14.3 g/l of lactose and 3FL 70 g/l of 3-FL, calculated lactose/3-FL ratio=0.22, conductivity 0.71 mS/cm. Calculated yields in the second NF/DF retentate: 3-FL 80.5%, lactose 13%.

The NF/DF retentates were combined to give a solution containing 3-FL in 94% yield with a reduced lactose/3-FL ratio of 0.1 compared to 0.43 in the initial UF permeate.

Example 10

2'-FL was made by fermentation using a genetically modified $E.\ coli$ cell of LacZ$^-$, LacY$^+$ phenotype, wherein said cell comprises a recombinant gene encoding an α-1,2-fucosyl transferase which is able to transfer the fucose of GDP-fucose to the internalized lactose and genes encoding a biosynthetic pathway to GDP-fucose. The fermentation was performed by culturing said cell in the presence of exogenously added lactose and a suitable carbon source, thereby producing 2'-FL which was accompanied with DFL and unreacted lactose in the fermentation broth (17 kg). As disclosed in Example 9, the fermentation broth was processed with UF/DF (17 l of water) to give an UF permeate (calculated total solids: 2.40 kg, 64% of which is 2'-FL, lactose/2'-FL ratio=0.11), which was processed by NF with Trisep UA60 membrane by concentrating first to ca 8 l at TMP=39 bar and T=45° C., followed by DF with 25 l of water. As a result, only 29% of lactose and most of the 2'-FL (82%) remained in the NF/DF retentate (calculated total solids: 1.54 kg, 82.5% of which is 2'-FL, lactose/2'-FL ratio=0.04).

The invention claimed is:

1. A method for separating a tri- or higher oligosaccharide from a disaccharide which are dissolved in a feed solution comprising:
(a) contacting the feed solution with a nanofiltration membrane with a molecular weight cut-off (MWCO) of 600-3500 Da ensuring the retention of the tri- or higher oligosaccharide and allowing at least a part of the disaccharide to pass, wherein the membrane is a piperazine-based polyamide membrane and comprises an active layer of polyamide, a MgSO$_4$ rejection of 50-90%, and a NaCl rejection not more than 30%; and
(b) collecting a retentate enriched in the tri- or higher oligosaccharide.

2. The method according to claim 1, wherein the membrane comprises a NaCl rejection lower than the MgSO$_4$ rejection.

3. The method according to claim 1, wherein the method comprises a diafiltration step between steps (a) and (b).

4. The method according to claim 1, wherein the polyamide nanofiltration membrane is a thin-film composite (TFC) membrane.

5. The method according to claim 1, wherein the membrane comprises a pure water flux of at least 50 l/m$^2$h.

6. The method according to claim 1, wherein the said tri- or higher oligosaccharide comprises the disaccharide in its structure.

7. The method according to claim 1, wherein the disaccharide is lactose.

8. The method according to claim 7, wherein the tri- or higher oligosaccharide is a human milk oligosaccharide (HMO).

9. The method according to claim 8, wherein the HMO is a neutral HMO.

10. The method according to claim 9, wherein the neutral HMO is a fucosylated HMO.

11. The method according to claim 9, wherein the neutral HMO is a non-fucosylated HMO.

12. The method according to claim 8, wherein the HMO is a sialylated HMO.

13. The method according to claim 8, wherein the HMO is produced by fermentation or enzymatically from lactose as precursor.

14. The method according to claim 13, wherein step a) is preceded by at least one of the following steps:
i) clarifying the aqueous medium from fermentation or enzymatic reaction to remove suspended particulates and contaminants, particularly cells, cell components, insoluble metabolites and debris from a fermentation process; and/or
ii) removing substantially all the proteins, as well as peptides, amino acids, RNA and DNA and any endotoxins and glycolipids that could interfere with the subsequent purification step, from the aqueous medium of the fermentation or enzymatic reaction.

15. The method according to claim 1, wherein the membrane comprises a MgSO$_4$ rejection of 80-90%.

16. The method according to claim 10 wherein the fucosylated HMO is selected from the group consisting of 2'-fucosyllactose (2'-FL), 3-fucosyllactose (3-FL), difucosyllactose (DFL) and lacto-N-fucopentaose I (LNFP-I).

17. The method according to claim 11, wherein the non-fucosylated HMO is selected from the group consisting of lacto-N-triose II, LNT, LNnT, pLNnH or pLNH II.

18. The method according to claim 12, wherein the sialylated HMO is 3'-sialyllactose (3'-SL) or 6'-sialyllactose (6'-SL).

* * * * *